(12) United States Patent
Dorn

(10) Patent No.: US 11,857,172 B2
(45) Date of Patent: Jan. 2, 2024

(54) VASCULAR CLOSURE DEVICE AND METHOD OF CLOSING A VASCULAR ACCESS HOLE USING SUCH A DEVICE

(71) Applicant: Angiomed GmbH & Co. Medizintechnik KG, Karlsruhe (DE)

(72) Inventor: Juergen Dorn, Neulussheim (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 0 days.

(21) Appl. No.: 17/770,275

(22) PCT Filed: Oct. 29, 2020

(86) PCT No.: PCT/EP2020/080396
§ 371 (c)(1),
(2) Date: Apr. 19, 2022

(87) PCT Pub. No.: WO2022/089744
PCT Pub. Date: May 5, 2022

(65) Prior Publication Data
US 2022/0361862 A1 Nov. 17, 2022

(51) Int. Cl.
*A61B 17/00* (2006.01)
(52) U.S. Cl.
CPC ...... *A61B 17/0057* (2013.01); *A61B 2017/00004* (2013.01); *A61B 2017/00623* (2013.01)
(58) Field of Classification Search
CPC ...... A61B 17/0057; A61B 2017/00659; A61B 2017/00592; A61B 2017/00597;
(Continued)

(56) References Cited

U.S. PATENT DOCUMENTS

| 5,647,857 A | * | 7/1997 | Anderson | A61F 2/958 604/161 |
| 5,755,769 A | * | 5/1998 | Richard | A61F 2/90 623/1.2 |

(Continued)

FOREIGN PATENT DOCUMENTS

| WO | 2005082256 A1 | 9/2005 |
| WO | 2007121747 A1 | 11/2007 |

(Continued)

OTHER PUBLICATIONS

PCT/EP2020/080396 filed Oct. 29, 2020 International Preliminary Report on Patentability dated Nov. 17, 2021.
J. Dorn, "Vascular Closure Device Background," Jun. 2022.

*Primary Examiner* — Dianne Dornbusch
(74) *Attorney, Agent, or Firm* — Rutan & Tucker LLP

(57) ABSTRACT

The present invention relates to a vascular closure device, comprising a self-expanding tubular vascular closure element, a retaining element surrounding the vascular closure element, the retaining element being arranged to hold the vascular closure element in the lumen of the retaining element in a configuration where the vascular closure element is not fully self-expanded, a tether that is threaded through the lumen of the retaining element, the tether being arranged so that, upon application of a first force to the tether which is greater than a threshold force, the tether disintegrates the retaining element so as to allow the vascular closure element to freely expand. It also relates to a system for delivering such a vascular closure device and to a method of closing a vascular access hole using a corresponding device.

13 Claims, 2 Drawing Sheets

(58) Field of Classification Search
CPC .. A61B 2017/0061; A61B 2017/00623; A61B 2017/00004; A61F 2/97; A61F 2/95; A61F 2002/9511; A61F 2002/9665; A61M 25/0668
See application file for complete search history.

(56) References Cited

U.S. PATENT DOCUMENTS

| | | | |
|---|---|---|---|
| 5,817,100 A | 10/1998 | Igaki | |
| 6,224,627 B1* | 5/2001 | Armstrong | A61F 2/90 623/1.13 |
| 6,254,628 B1* | 7/2001 | Wallace | A61B 17/1214 606/108 |
| 6,398,758 B1* | 6/2002 | Jacobsen | A61B 17/22 604/11 |
| 6,447,540 B1 | 9/2002 | Fontaine et al. | |
| 6,984,242 B2 | 1/2006 | Campbell et al. | |
| 8,066,756 B2 | 11/2011 | Rasmussen et al. | |
| 8,439,961 B2 | 5/2013 | Jagger et al. | |
| 8,641,752 B1 | 2/2014 | Holm et al. | |
| 8,652,193 B2 | 2/2014 | Dorn | |
| 8,784,466 B2 | 7/2014 | Igaki | |
| 8,852,257 B2 | 10/2014 | Liu et al. | |
| 8,906,081 B2 | 12/2014 | Cully et al. | |
| 8,961,582 B2 | 2/2015 | Holm et al. | |
| 9,072,590 B2 | 7/2015 | Wang et al. | |
| 9,226,839 B1 | 1/2016 | Kariniemi et al. | |
| 9,364,361 B2 | 6/2016 | Duong et al. | |
| 9,375,215 B2 | 6/2016 | Cully et al. | |
| 9,381,018 B2 | 7/2016 | Cully et al. | |
| 9,402,755 B2 | 8/2016 | Norris et al. | |
| 2002/0099431 A1 | 7/2002 | Armstrong et al. | |
| 2006/0015171 A1 | 1/2006 | Armstrong | |
| 2008/0221616 A1 | 9/2008 | Ginn et al. | |
| 2008/0255580 A1* | 10/2008 | Hoffman | A61F 2/97 606/108 |
| 2009/0254169 A1* | 10/2009 | Spenser | A61F 2/97 623/1.12 |
| 2011/0087270 A1 | 4/2011 | Penner et al. | |
| 2011/0106131 A1 | 5/2011 | Argentine | |
| 2011/0213449 A1* | 9/2011 | Ginn | A61B 17/0057 623/1.11 |
| 2012/0109281 A1 | 5/2012 | Papp | |
| 2012/0123511 A1 | 5/2012 | Brown | |
| 2012/0165915 A1* | 6/2012 | Melsheimer | A61F 2/9661 623/1.11 |
| 2012/0172887 A1 | 7/2012 | Hatfield | |
| 2013/0158524 A1 | 6/2013 | Fargahi | |
| 2013/0245743 A1* | 9/2013 | Norris | A61F 2/95 623/1.11 |
| 2014/0135894 A1* | 5/2014 | Norris | A61F 2/966 623/1.11 |
| 2014/0188210 A1* | 7/2014 | Beard | A61F 2/97 623/1.12 |
| 2014/0277359 A1 | 9/2014 | Slazas et al. | |
| 2014/0379064 A1 | 12/2014 | Pacetti et al. | |
| 2014/0379065 A1 | 12/2014 | Johnson et al. | |
| 2015/0088240 A1 | 3/2015 | Lam et al. | |
| 2019/0038442 A1 | 2/2019 | Milisav et al. | |
| 2019/0224448 A1 | 7/2019 | Connors et al. | |

FOREIGN PATENT DOCUMENTS

| | | |
|---|---|---|
| WO | 2009050265 A1 | 4/2009 |
| WO | 2009088440 A1 | 7/2009 |
| WO | 2010062693 A2 | 6/2010 |
| WO | 14201105 A2 | 12/2014 |

\* cited by examiner a)

b)

VASCULAR CLOSURE DEVICE AND METHOD OF CLOSING A VASCULAR ACCESS HOLE USING SUCH A DEVICE

PRIORITY

This application is a U. S. national stage application of International Application No. PCT/EP2020/080396, filed Oct. 29, 2020, which is incorporated by reference in its entirety into this application.

TECHNICAL FIELD

The present invention relates to a device that is to be used for closing an opening in a blood vessel (i.e., a vascular closure device). It furthermore relates to a system for deploying such a vascular closure device and to a method of closing an opening in a blood vessel using such a device.

TECHNICAL BACKGROUND

During endovascular surgery, a surgeon typically penetrates into a patient's vasculature through a vascular access hole that establishes a connection between the lumen of the patient's blood vessels with the surroundings. Through this vascular access hole, devices such as catheters are introduced into the vasculature and are advanced to the treatment site.

After the surgery has been completed, the devices that have been introduced into the vasculature are extracted but the vascular access hole remains. To stop bleeding, this vascular access hole needs to be closed. In order to close the vascular access hole, prior art documents such as U.S. Pat. No. 9,375,215 B2 report the placing of a vascular stent graft on the inside of the blood vessel that pushes against the vascular access hole and thus closes off that vascular access hole from the inside.

It is, however, to be noted that this technology can also be used in applications outside of the surgical theatre, for example in the treatment of accidents on the road or on the battlefield, where it is necessary to urgently stop bleeding in critical situations.

SUMMARY OF THE INVENTION

It was realised that with prior art vascular closure devices, there still exists a need for an improvement. In particular, it has been found that haematoma of a diameter of more than 5 cm, pseudo-aneurysms, arteriovenous fistulae, access-site related bleeding, acute ipsilateral leg ischaemia and other complications sometimes arise which are undesirable and which in some cases require further surgical/interventional treatment. It has also been found that the risk of creating local infections needs to be minimised. The inventors have further realised the need to simplify the structure of the vascular closure device.

The present invention aims at alleviating or solving at least some of the previously mentioned problems.

The invention is defined by independent claims 1, 10, and 11. Optional features are defined in the respective dependent claims.

According to claim 1, a vascular closure device comprises a self-expanding tubular vascular closure element. Such a self-expanding tubular vascular closure element can, for example, take the form of a stent that is at least partially covered, with the covering being arranged to be pushed against the vascular access hole to thereby close that hole. This pushing would then serve to close off and to thus seal the vascular access hole from the inside. Generally speaking, a vascular closure element can be any tube-shaped element that has a sufficiently impervious wall so as to seal a vascular access hole against blood leakage. By the vascular closure element being self-expanding, it is meant that the vascular closure element will, when heated to a temperature of around the human body temperature, expand by itself without the need for, say, an inflatable balloon or some other kind of external means for expanding it. This expansive force pushes the covering of the vascular closure element against the vascular access hole to close the vascular access hole. Further, this expansive force anchors the vascular closure element inside the patient's blood vessel and thus prevents it from moving in the same way a typical stent or stent graft is anchored inside a blood vessel by pushing against the walls of the blood vessel.

There is furthermore provided a retaining element that can have the form of a tube that is, in embodiments, made of a single layer. In embodiments, the tube has a circular cross-section. This retaining element surrounds the vascular closure element with the vascular closure element being arranged inside the lumen of the retaining element and retains the vascular closure element in a configuration where the vascular closure element is not fully self-expanded. That is, the retaining elements restrains the vascular closure element and will hold the vascular closure element in a configuration in which the vascular closure element is not fully self-expanded. This restraining function will also function whilst the assembly of the vascular closure element and the retaining element is inserted into a patient's vasculature—i.e., the retention force of the retaining element is sufficiently strong so as to prevent the self-expansion of the vascular closure element whilst the retaining element is positioned so as to surround the vascular closure element.

Furthermore, a tether is provided. This tether is arranged so that, upon application of a first force to the tether that is larger than a threshold force, the retaining element will be disintegrated to such an extent that the vascular closure element can freely expand. Put differently, in such a configuration, the retaining element will no longer hold the vascular closure element in the non-expanded configuration. In the present context, the word "disintegrate" means that the retaining element loses its shape to such an extent that it is no longer capable of holding the vascular closure element in the non-expanded configuration. For example, in the case of the vascular closure element being a tube that consists of a single sheet that is wrapped into a tubular shape, this could mean that the tube is split lengthwise. If the tube is to consist of a fabric made of one or more woven/knitted threads, "disintegrating" means that the thread(s) are rearranged so that they no longer constitute a fabric that could restrain the vascular closure element. In embodiments, this rearrangement could mean that the thread(s) are entirely disentangle, but it is to be noted that a complete disentanglement is not necessary.

With a thus configured vascular closure device, it becomes possible to simplify the structure. In particular, compared with prior art devices such as U.S. Pat. No. 9,375,215 B2, it is possible to use a much simpler retaining element which can have the form of a simple tube. Since one uses the tether to disintegrate the retaining element, one does not need to provide the otherwise rather complicated structure shown in U.S. Pat. No. 9,375,215 B2, where a thread is threaded through a series of pre-fabricated openings. Accordingly, a corresponding vascular closure device is easier to manufacture.

As pointed out before, the tether serves a dual function. When a force is applied to the tether that is less than the threshold force, the tether will not disintegrate the retaining element. Thus, if a sufficiently small force is applied, the vascular closure element will be moved. Only upon application of a second, larger force that exceeds the threshold force will the tether disintegrate the retaining element. Therefore, the tether has a dual purpose of serving, for a small enough force, as a positioning element for the assembly of the retaining element and the vascular closure element, and serving, for a larger force, as a disintegrating unit for disintegrating the retaining element to thereby allow for (further) expansion of the vascular closure element.

In embodiments, the tether is threaded through the lumen of the retaining element and, in further embodiments, extends between the vascular closure element and the retaining element. The tether is arranged so that, upon application of a first force to the tether which is greater than a threshold force, the tether will cut through the retaining element so as to allow the vascular closure element to freely self-expand. That is, when the vascular closure element is held in place (for example by the vascular closure element being pulled against the walls of a blood vessel), and when a sufficiently strong force is applied to the tether, the tether will cut through the retaining element to thereby allow for a self-expansion of the vascular closure element. If, on the other hand, the force is small than the threshold force, the tether will not cut through the retaining element and will instead move the assembly of the retaining element and of the vascular closure element. Such a system is easy to implement, since the disintegration of the retaining element is achieved by a comparatively simple cutting action.

In an embodiment, the tether is arranged so that the tether extends from a first longitudinal end of the retaining element to an opposite second longitudinal end of the retaining element. By "longitudinal", we mean the axial direction of the retaining element (i.e., given that the retaining element is typically tubular, the axis of that tube). Both ends of the tether are arranged outside of the assembly of the vascular closure element and the retaining element. Since both ends of the tether are arranged outside of the assembly of the vascular closure element and the retaining element, with, in embodiments, the two ends of the tether being arranged at opposite longitudinal ends of the retaining element, it becomes possible to easily centre the retaining element and the vascular closure element by pulling at both ends of the tether at the same time. If the two ends of the tether are led through the vascular access hole, this will then centre the retaining element on the vascular access hole.

If the vascular closure element is arranged so that those portions of that vascular closure element that can serve so as to close the vascular access hole are arranged so as to be covered by the retaining element, this will allow for positioning the vascular closure element so that the vascular closure element closes the vascular access hole. Accordingly, since it is comparatively easy to position the vascular closure element simply by exerting a pull force on the two ends of the tether, the vascular closure device is particularly user friendly.

In that context, in embodiments, the two ends of the tether are joined together so that the tether forms a loop. Since they are joined together, it becomes particularly easy to apply a pull force to it, namely by simply pulling on the loop-shaped tether. As pointed out previously, this allows for easily positioning the vascular closure element.

In embodiments, there is furthermore provided a pullout-tether. This pullout-tether is coupled to the retaining element and is arranged so that, once the retaining element has been cut for example by means of applying a sufficiently high force to the tether, the retaining element can be easily withdrawn from the patient's vasculature by being pulled, using the pullout-tether, through the vascular access hole. Accordingly, a corresponding vascular closure device is particularly user friendly.

In embodiments, the retaining element is made of PET (polyethylene terephthalate). Such materials are well characterised and have found widespread use in endovascular surgery. Further, in PET, the application of a sufficiently high force to the tether will lead to a crack propagating through the PET sleeve, which improves the cutting behaviour.

In other embodiments, the retaining element comprises a knitted sleeve arranged so as to surround the vascular closure element. The tether is coupled to the knitted sleeve so that upon application of the first force larger than the threshold force, the knitted sleeve disintegrates so as to allow the vascular closure element to expand. In such a way, the tether would be coupled to the loops of the knitted fabric of the sleeve. The knitting would be such that the fabric disintegrates when the tether is pulled. In such a configuration, since the tether and the retaining element are made of the same thread, the number of parts can be reduced.

In that context, in further embodiments, the knitted sleeve comprises a thread made of UHMWPE (ultra-high-molecular-weight polyethylene), such as Dyneema®. Since thus, the fabric is knitted from a thread made of UHMWPE, the knitted fabric is particularly adapted for use in surgery.

In embodiments, the vascular closure element comprises a stent graft. The stent graft may be covered by a covering material along the entirety of the base stent, but it is sufficient if base stent is only partially covered. That is, the stent graft is not necessarily covered along its whole length but could, in embodiments, only be covered along parts of its longitudinal and/or circumferential extent. Such stent grafts are well characterised and widely used in endovascular surgery, which means that one can apply the expertise in the manufacture of such devices to thereby produce a highly reliable vascular closure device. The base stent can, in embodiments, have a sufficiently coarse mesh so that it can, if desired, be penetrated post-placement using a syringe or other kind of medical and/or surgical device. As a covering material for the stent graft, it is conceivable to use ePTFE.

In embodiments, the vascular closure element comprises a bioresorbable material. A bioresorbable material is a material that will dissolve after some time when provided inside a patient's vasculature. Examples of such bioresorbable materials are polylactic acids (PLLA). Other types of material that can be used are magnesium, which could be in the form of a web or a foil. In embodiments, the bioresorbable material is arranged as a patch on the surface of the vascular closure element on that position of the vascular closure element that is to be used for closing the vascular access hole. By having the vascular closure element made of a bioresorbable material, the vascular closure element will dissolve over time and typically over the course of several days and weeks. Since during that timeframe, the vascular access hole though normally has been closed by means of the natural healing processes of the human body, the vascular closure element will reduce the cross-section of the vascular closure device and will thus reduce its effect on the blood vessel the vascular closure element is implanted in. In further embodiments, substantially the entire vascular closure element is made of a bioresorbable material (i.e. the meshwork of the base stent as well as the material that is designed for closing the wound). In that respect, PLLA is particularly useful since it is bioresorbable and can be used for manufacturing self-expanding stents.

In embodiments, the tether is arranged so that between the first and the second longitudinal end of the retaining element, the tether extends entirely on the inside of the retaining element. That is, the tether is not threaded through the retaining element so that it partially extends inside and partially outside the retaining element. Such a vascular closure device is easier to manufacture.

In embodiments, the tether is arranged between those parts of the vascular closure element that are suitable for closing off (sealing) the vascular access hole and the retaining element. This allows for a particularly easy positioning of the vascular closure device relative to the vascular access hole.

According to another aspect of the invention, there is provided a system for delivering a vascular closure device as discussed previously. This system comprises a catheter for introduction into a patient's blood vessels. This catheter is arranged so that the catheter can deliver the vascular closure device into the patient's blood vessels by means of first introducing the catheter sheath into a blood vessel (e.g. through the vascular access hole) and then advancing the vascular closure device through that sheath. The assembly of the vascular closure element and of the retaining element is arranged at a distal end of the catheter so as to allow for easy deployment.

According to another aspect of the present invention, a method of closing vascular access hole inside a blood vessel is provided. This method comprises deploying the vascular closure device as discussed previously inside a patient's vasculature through the vascular access hole, so that the tether extends to the outside of the patient's body through the vascular access hole. Subsequently, a first pull force less than the threshold force is applied on the tether. This serves to pull the assembly of the vascular closure element and the retaining element against the vascular wall adjacent the vascular access hole so as to position the parts of the vascular closure element that are meant to seal the vascular access hole against that hole. After that step, a second pull force is applied that is greater than the threshold force on the tether. By the application of that force, the tether disintegrates the retaining element. Once the retaining element has been disintegrated, the vascular closure element is released from the retaining element and can then self-expand. During that self-expansion step, the vascular closure element will push against the walls of the blood vessel having the vascular access hole and will thereby seal the vascular access hole. Accordingly, the vascular access hole is sealed. Such a method is easier to perform for a surgeon and, in particular, in embodiments reduces the amount of tether that needs to be pulled out compared with U.S. Pat. No. 9,375,215 B2.

In embodiments, the method further comprises withdrawing the tether from the patient's body. Using that method, it is prevented that the tether unnecessarily interferes with the patient's body.

In further embodiments, the method further comprises removing the disintegrated retaining element from the patient's body, which avoids that the retaining element that has been disintegrated interferes with the patient's body.

DETAILED DESCRIPTION OF THE DRAWINGS

Figure 1:
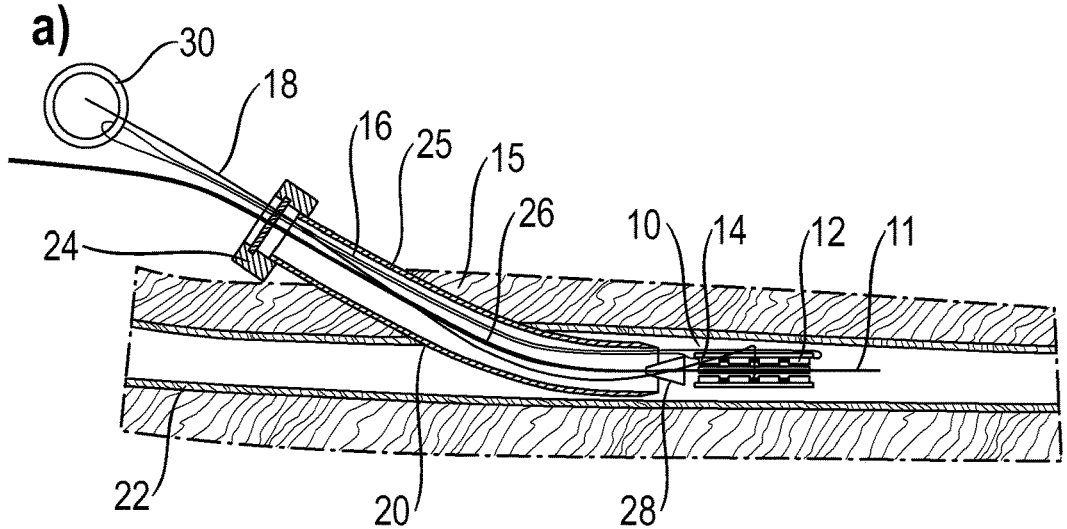
FIG. 1 shows a system for delivering a vascular closure device according to an embodiment in a delivery configuration.
Figure 1:
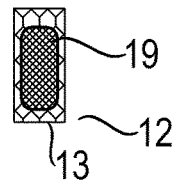

FIG. 1 shows, in subfigure a), a vascular closure device 10 during a first stage of deployment in a blood vessel 22. The blood vessel 22, which has a vascular access hole 15 that connects the blood vessel 22 to the outside of the patient's body and that may have been created during a surgery, for example an endovascular surgery, has arranged therein a catheter 20. The blood vessel 22 is, for example, the arteria femoralis. This catheter 20 comprises a sheath (introducer/guide sheath) 25 that extends through the vascular access hole 15 into the blood vessel 22. The distal end of the sheath 25 is arranged inside the blood vessel 22, and the proximal end is arranged outside of the blood vessel and comprises a gate 24 for the selective introduction and removal of components into and from the sheath 25. In that context, the word "proximal" refers to a direction along the sheath 25 towards the surgeon, and "distal" refers to the opposite direction away from the surgeon.

As can be seen in FIG. 1, the vascular closure device 10 has been positioned inside the blood vessel 22. This vascular closure device 10 comprises a vascular closure element (stent graft) 12 that is shown in more detail in FIG. 1b). Around that vascular closure element 12, a tube-like retaining element 14 made of a single layer PET sheath is wrapped so as to retain the vascular closure element 12 in the non-fully-expanded configuration. In that configuration, the assembly of the vascular closure element 12 and of the retaining element in a sheath form can be arranged inside the lumen of the sheath 25, which is the delivery configuration of the vascular closure device 10 (not shown).

Also shown is a pusher wire 11 that extends through the lumen of the vascular closure element 12 and through the lumen of the sheath 25. Provided proximally relative to the stent graft 12 is a pusher cone 28 that is dimensioned so that the pusher cone 28 can push the vascular closure element 12 out of the lumen of the sheath 25. Such a pusher wire 11 can be made of nitinol and can have, in embodiments, a thickness of from 0.02" to 0.035". The pusher wire 11 allows for pushing the vascular closure element 12 out of the lumen of the sheath 25 during deployment.

A tether 16 that can be made of a metal wire extends through the sheath 25 and is sandwiched between the vascular closure element 12 and the retaining element 14. Tether 16 could also be referred to as a loop split tether. The two ends of the tether 16, which could, in embodiments, also be referred to as a loop split wire, are lead through the lumen of the sheath 25 to a position beyond the proximal end of the sheath 25 where they are joined together. A pull ring 30 is arranged so that the tether 16 is slidably threaded through it. The pull ring 30 can be used for applying pull force onto the tether 16. It is to be noted that the pull ring 30 is entirely optional and does not need to be present. It is also to be noted that the pull ring 30 does not need to have a circular shape. Through pulling that tether 16, the vascular closure element 12 can be positioned adjacent the vascular access hole 15, as will be discussed in more detail below, and can be also released from the retaining element 14. The details of this positioning and release will be discussed subsequently with reference to FIGS. 2-5.

Furthermore, a pullout-tether 18 is provided that could also be referred to as a split sheath removal line. This pullout-tether 18 is connected to the retaining element 14 and is led through the interior of the sheath 25 so that the pullout-tether 18 extends beyond the proximal end of the sheath 25. As will be discussed more fully when discussing the subsequent drawings, this pullout-tether 18 can be used for removing the cut retaining element 14 from the patient's vasculature.

FIG. 1b) shows in more detail the structure of the vascular closure element (vascular plug) 12. As can be seen from that drawing, a base stent 13 is provided which has arranged thereon a patch 19 that can, in embodiments, be made of polylactic acid (PLLA). However, as discussed previously, other materials can also be used. The base stent 13 itself is made of a self-expanding material. In embodiments, nitinol was used for the base stent 13, which was cut with a femto laser technology for selective material ablation. In embodiments, the base stent 13 had an expanded diameter of about 9-12 mm and was covered on one circumferential half with a PLLA patch 19 that had a length of about 10 mm. Such a length has been found to cover, with a great safety margin, the puncture access sites in femoral arteries.

In the presently shown embodiment in FIG. 1a), the tether 18 is looped between the PLLA patch 19 and the retaining element 14. This allows for a more accurate positioning of that patch adjacent the vascular access hole 15, since pulling on the tether 18 will automatically position the patch 19 adjacent the vascular access hole 15.

In embodiments, a 5 F outer diameter catheter was used as the sheath 25. An example system was a Halo 1 catheter sheath provided Becton Dickinson and Company, which has a 4 F inner diameter.

Figure 2:
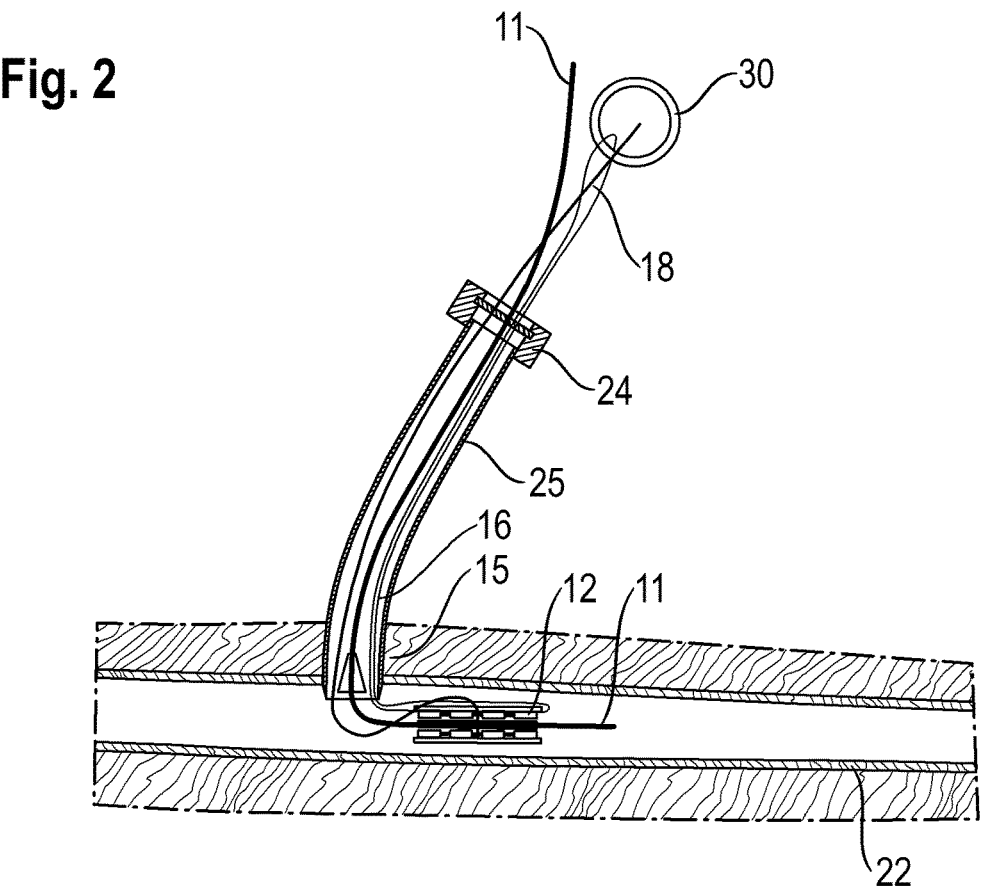
FIG. 2 shows the system according to FIG. 1 and a consideration where the catheter is in the process of being withdrawn.

Whilst FIG. 1a) shows a configuration where the assembly of the vascular closure element 12 and retaining element 14 has just been pushed out of the distal end of the catheter 20, FIG. 2 shows a configuration that happens somewhat later during the deployment of the vascular closure element 12. As can be seen from FIG. 2, the sheath 25 has been largely withdrawn from the blood vessel 22 whilst still facilitating haemostasis. Whilst the sheath 25 still extends through the vascular access hole 15, it extends much less into the blood vessel 22 then in the configuration shown in FIG. 1a). In the configuration shown in FIG. 2, the vascular closure element 12 is still restrained by the retaining element 14 so that its cross-sectional diameter is significantly less than the diameter of the blood vessel 22. Accordingly, the vascular closure element 12 can move freely inside that blood vessel 22 and can thus, by means of applying a pull force to the tether 16, be moved in its position inside the blood vessel 22.

Figure 3:
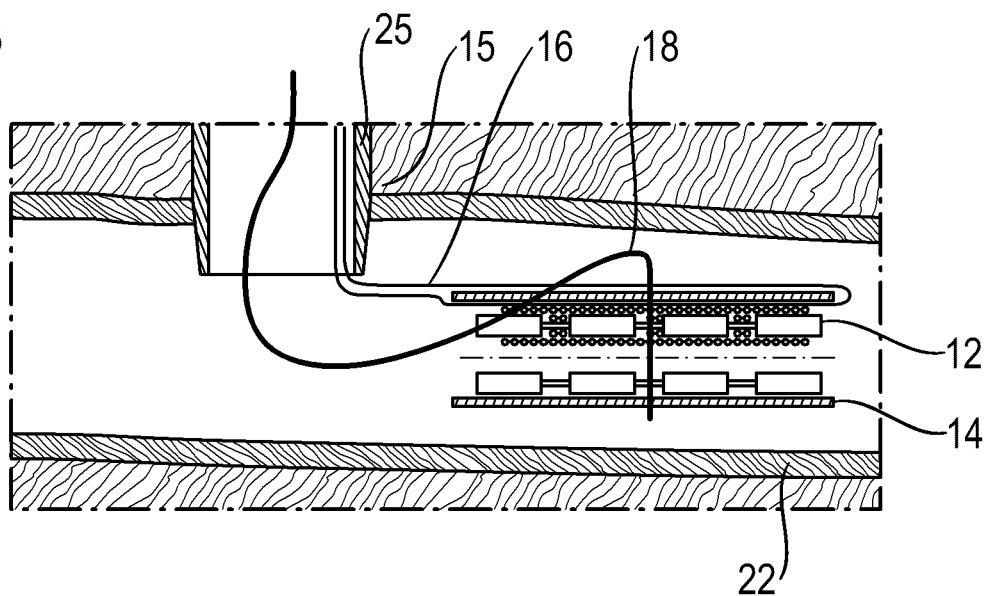
FIGS. 3 and 4 show further steps in the deployment of the vascular closure element of the system according to FIGS. 1 and 2.

FIG. 3 shows the next step in the deployment of the vascular closure element 12. As can be seen from that figure, the tether 16 extends out of the distal end of the sheath 25 and is sandwiched between the vascular closure element 12 (more precisely, the PLLA patch 19) and the retaining element 14. However, we can be seen from that figure, the pusher wire 11 has been withdrawn from the blood vessel 22.

Figure 4:
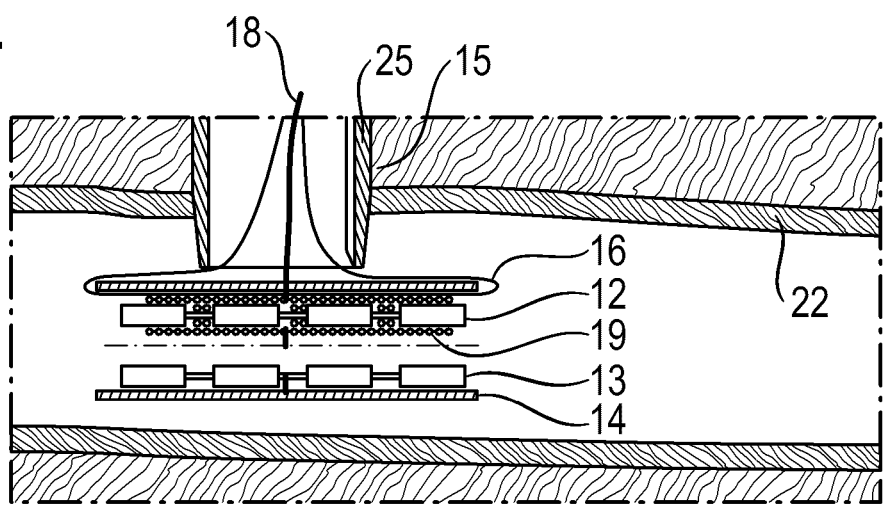

When now applying a pulling force to the pull ring 30, the tether 16 is pulled through the sheath 25 which transitions the system from the configuration shown in FIG. 3 to that shown in FIG. 4. Due to the force that is applied to the tether 16 being symmetric, the vascular closure element 12 gets positioned so that the vascular closure element 12 is centred on the vascular access hole 15. Accordingly, since the tether 16 is arranged so that the tether 16 is sandwiched between the retaining element 14 and the patch 19, the patch 19 is arranged adjacent to the vascular access hole 15 and is thus adequately positioned for closing that vascular access hole 15 from the inside. However, as can also be seen from FIG. 4, in that configuration, the vascular closure element has still too small a diameter to be fixed in position relative to the blood vessel 22 thanks to the presence of the retaining element 14. That is, if the tether 16 (as well as the pullout-tether 18) were not present, the assembly of the vascular closure element 12 and the retaining element 14 would move freely inside the blood vessel 22, which is undesirable if one wants to close the vascular access hole 15.

When the configuration that is shown in FIG. 4 has been reached, the surgeon would then apply a stronger pull force on the tether 16. This pull force would lead to the tether 16 cutting through the retaining element 14 at those places where the tether 16 is in contact with the retaining element 14.

Since the tether 16 extends along the entire length of the retaining element 14, the tether 16 will cut the entire length of the retaining element 14. In consequence, the thus cut retaining element 14 would no longer exert a restraining force on the self-expansion of the vascular closure element 12. This vascular closure element 12 will then self-expand due to the vascular closure element 12 being exposed to the patient's blood stream and thus push against the walls of the blood vessel 22. The vascular closure element 12 will thereby push the patch 19 against the vascular access hole 15 to thereby seal the vascular access hole 15. Subsequently, the surgeon would then withdraw the tether 16 and also, using the pullout-tether 18, the cut remainder of the retaining element 14 from the patient's body via the sheath 25 of the catheter 20.

Figure 5:
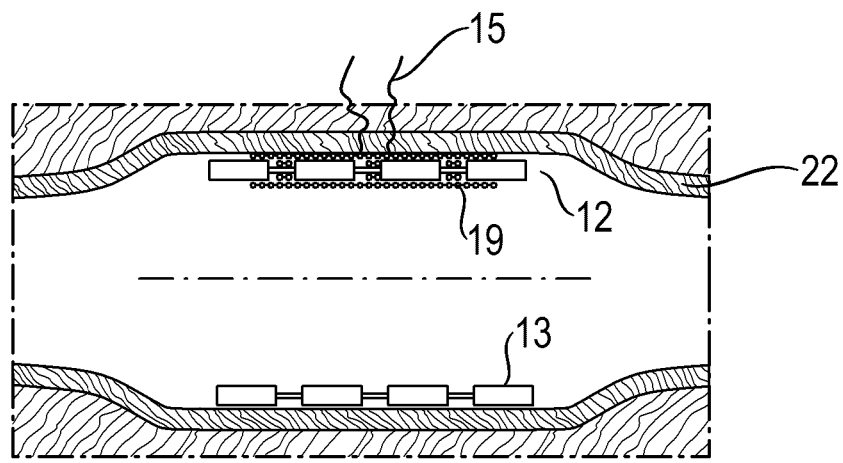
FIG. 5 shows the fully deployed vascular closure element.

In that way, the configuration shown in FIG. 5 is achieved where the vascular closure element 12 has sufficiently self-expanded so as to push the patch 19 against the vascular access hole 15 that is shown, in the configuration shown in FIG. 5, as having partially healed. The thus closed vascular access hole 15 is thus sealed from the inside so that blood cannot leak out of it. Since the patch 19 has been made of a bioresorbable material, the patch 19 will dissolve with time so that the cross-section of the vascular closure element 12 will be reduced and will finally only be the cross-section of the base stent 13, which therefore reduces the impact on blood flowing through the blood vessel 22.

It is to be noted that the naturally occurring blood pressure will also serve to push the patch 19 against the vascular access hole 15 which therefore improves the sealing and will reduce bleeding. Further, since after the placement of the vascular closure element 12, and the withdrawal of the tether and the pullout-tether 18, there are no components that extend to the outside of the blood vessel 22, the risk of an infection is reduced. It is additionally believed that having such a way of closing the wound will reduce the risk of subcutaneous bleeding as well as the creation of haematomas and pseudo-aneurysms. Additionally, due to the absence of small parts and a sealing agent, which might be dislodged, there is a smaller risk of an ipsilateral leg ischaemia.

The invention claimed is:

1. A vascular closure device, comprising:
   a self-expanding tubular vascular closure element comprising a patch configured to close a vascular access hole,
   a retaining element surrounding the vascular closure element, the retaining element being arranged to hold the vascular closure element in a lumen of the retaining element in a configuration where the vascular closure element is not fully expanded, a tether being arranged lengthwise to extend from a first longitudinal end of the retaining element to a second longitudinal end of the retaining element, opposite the first longitudinal end of the retaining element so that, upon application of a first force to the tether which is greater than a threshold force, the tether disintegrates a portion of the retaining element to such an extent that the vascular closure element can freely expand; and a pullout-tether coupled to the retaining element, the pullout-tether being arranged circumferentially around a mid-portion between a proximal end and a distal end of the retaining element for withdrawing the retaining element from a patient's vasculature once the portion of the retaining element has been disintegrated.

2. The vascular closure device according to claim 1, wherein a portion of the tether is threaded through the lumen of the retaining element, the tether being arranged so that, upon application of the first force to the tether which is greater than the threshold force, the portion of the tether cuts through the portion of the retaining element so as to allow the vascular closure element to freely expand.

3. The vascular closure device according to claim 2, wherein a first end of the tether and a second end of the tether are arranged outside of an assembly of the vascular closure element and the retaining element, the portion of the tether being disposed between the first end of the tether and the second end of the tether.

4. The vascular closure device according to claim 3, wherein the first end of the tether is joined together with the second end of the tether.

5. The vascular closure device according to claim 2, wherein the portion of the tether extends entirely on an inside of the retaining element.

6. The vascular closure device according to claim 2, wherein the tether is routed between a portion of the vascular closure element that is suitable for sealing the vascular access hole and the retaining element.

7. The vascular closure device according to claim 1, wherein the retaining element is made of polyethylene terephthalate ("PET").

8. The vascular closure device according to claim 1, wherein the retaining element comprises a knitted sleeve arranged so as to surround the vascular closure element, the tether being coupled to the knitted sleeve so that upon application of the first force larger than the threshold force, the portion of the retaining element disintegrates so as to allow the vascular closure element to expand.

9. The vascular closure device according to claim 8, wherein the knitted sleeve comprises a thread made of ultra-high-molecular-weight polyethylene ("UHMWPE").

10. The vascular closure device according to claim 1, wherein the vascular closure element comprises a stent graft.

11. The vascular closure device according to claim 1, wherein the vascular closure element comprises a bioresorbable material.

12. A system for delivering the vascular closure device according to claim 1, comprising:

a catheter for introduction into a patient's blood vessels, wherein the vascular closure element and the retaining element are arranged at a distal end of the catheter.

13. The vascular closure device according to claim 1, wherein the patch comprises a bioresorbable material.

* * * * *